United States Patent
Schicho (10) Patent No.: US 11,324,535 B2
(45) Date of Patent: May 10, 2022

(54) NEEDLE ASSEMBLY FOR RELIEVING A PNEUMOTHORAX

(71) Applicant: Universität Regensburg—Universitätsklinikum, Regensburg (DE)

(72) Inventor: Andreas Johannes Schicho, Regensburg (DE)

(73) Assignee: Universität Regensburg—Universitätsklinikum, Regensburg (DE)

( * ) Notice: Subject to any disclaimer, the term of this patent is extended or adjusted under 35 U.S.C. 154(b) by 65 days.

(21) Appl. No.: 16/756,763

(22) PCT Filed: Nov. 12, 2018

(86) PCT No.: PCT/EP2018/080968
§ 371 (c)(1),
(2) Date: Apr. 16, 2020

(87) PCT Pub. No.: WO2019/096747
PCT Pub. Date: May 23, 2019

(65) Prior Publication Data
US 2021/0093352 A1    Apr. 1, 2021

(30) Foreign Application Priority Data
Nov. 20, 2017 (EP) .................... 17202544

(51) Int. Cl.
  *A61B 17/34* (2006.01)
  *A61B 17/00* (2006.01)
(52) U.S. Cl.
  CPC ...... *A61B 17/3421* (2013.01); *A61B 17/3415* (2013.01); *A61B 17/3474* (2013.01);
(Continued)

(58) Field of Classification Search
  CPC ...... A61B 2017/00809; A61B 17/3421; A61B 17/3415; A61B 17/3474; A61B 17/3496;
(Continued)

(56) References Cited

U.S. PATENT DOCUMENTS

| 5,104,382 A | * | 4/1992 | Brinkerhoff | ....... A61B 17/3496 604/164.12 |
| 5,401,247 A | * | 3/1995 | Yoon | .................. A61B 10/0233 604/164.12 |

(Continued)

FOREIGN PATENT DOCUMENTS

| CN | 2149904 Y | 12/1993 |
| CN | 2395728 Y | 9/2000 |

(Continued)

OTHER PUBLICATIONS

International Searching Authority/European Patent Office, International Search Report and Written Opinion of the International Searching Authority, Application No. PCT/EP2018/080968, dated Jan. 23, 2019, 14 pages.

*Primary Examiner* — Tan-Uyen T Ho
*Assistant Examiner* — Bridget E. Rabaglia
(74) *Attorney, Agent, or Firm* — Sunstein LLP (57) ABSTRACT

A needle assembly (10) for relieving a pneumothorax and/or a hemothorax, the needle assembly (10) comprising a canula (12), the canula (12) comprising: a distal end portion (20) comprising a cutting end (22) for puncturing a thoracic cavity wall (24), a proximal end portion (14) for removing a fluid or gas from a thoracic cavity (28), a first curved portion (18) between the distal end portion (20) and the proximal end portion (14), an intermediate portion (16) between the first curved portion (18) and the proximal end portion (14), and a first fixing bulge (42) arranged between the first curved portion (18) and the intermediate portion (16), wherein an outer diameter of the canula (12) at the first (Continued)

fixing bulge (42) is increased with respect to the diameter (D1) of the intermediate portion (16), said first fixing bulge (42) being arranged such as to be placed at or close to the inner surface (24) of the thoracic cavity wall (24*i*), when the canula (12) is inserted for relieving the pneumothorax, such as to prevent or to reduce the risk that the canula (12) inadvertently slides out of its inserted position.

19 Claims, 6 Drawing Sheets

(52) U.S. Cl.
CPC .............. *A61B 2017/00809* (2013.01); *A61B 2017/00862* (2013.01); *A61B 2017/3456* (2013.01)

(58) Field of Classification Search
CPC .............. A61B 17/3494; A61B 17/34; A61B 2017/00862; A61B 17/3478; A61B 17/3486; A61B 17/3488; A61B 2017/3437; A61B 2017/3427; A61B 17/3427; A61B 17/32053; A61M 2025/0089; A61M 1/04; A61M 2025/0233; A61M 2025/028; A61M 2029/0252; A61M 2039/0276; A61M 39/0247
USPC ......... 604/164.01, 164.04, 164.06, 264, 272, 604/274; 606/185, 184
See application file for complete search history.

(56) References Cited

U.S. PATENT DOCUMENTS

| | | | | |
|---|---|---|---|---|
| 5,509,909 | A * | 4/1996 | Moy | A61B 17/3415 |
| | | | | 604/170.03 |
| 6,638,253 | B2 * | 10/2003 | Breznock | A61M 27/00 |
| | | | | 128/207.29 |
| 8,343,045 | B2 * | 1/2013 | Swinehart | A61B 17/00234 |
| | | | | 600/184 |
| 8,506,577 | B2 * | 8/2013 | Tanaka | A61K 9/007 |
| | | | | 606/108 |
| 2006/0079838 | A1 * | 4/2006 | Walker | A61M 25/04 |
| | | | | 604/104 |
| 2010/0204707 | A1 | 8/2010 | Tanaka et al. | |
| 2015/0150593 | A1 * | 6/2015 | Trovato | A61M 1/84 |
| | | | | 606/108 |
| 2015/0265777 | A1 * | 9/2015 | Whitley | A61B 17/3474 |
| | | | | 604/512 |
| 2016/0022312 | A1 | 1/2016 | Tang et al. | |
| 2017/0035509 | A1 * | 2/2017 | Chen | A61B 17/3474 |
| 2019/0314561 | A1 * | 10/2019 | Rhee | A61M 1/04 |

FOREIGN PATENT DOCUMENTS

| | | |
|---|---|---|
| CN | 2780205 Y | 5/2006 |
| EP | 2792321 A1 | 10/2014 |
| GB | 2524580 A | 9/2015 |
| WO | WO 2010/087690 A1 | 8/2010 |

* cited by examiner

NEEDLE ASSEMBLY FOR RELIEVING A PNEUMOTHORAX

CROSS-REFERENCE TO RELATED APPLICATIONS

This application is the national phase entry of International Patent Application No. PCT/EP2018/080968 filed on Nov. 12, 2018, and claims the benefit of EP Patent Application No. 17202544.7 filed Nov. 20, 2017, the disclosures of which are incorporated herein by reference in their entirety.

FIELD OF THE INVENTION

The present invention is in the field of medical technology. More precisely, the present invention relates to a needle assembly for relieving a pneumothorax.

BACKGROUND

The lung of a human retains its shape through a vacuum in the pleural cavity between the visceral and the parietal pleura, i.e. between the lung and the thoracic cavity wall. Thus, the movement of the thoracic cavity wall or the thoracic diaphragm can inflate or deflate the lung during the respiratory act. A pneumothorax is a medical condition, wherein air or a liquid, such as blood (hemothorax), chyle (chylothorax) or transudate (hydrothorax), collects in the pleural cavity and can thereby lead to the collapse of the vacuum in the pleural cavity. In some cases, a puncture of the thoracic cavity wall by a foreign object or a broken rib can even lead to a buildup of an overpressure in the pleural cavity, referred to as a tension pneumothorax.

The collapse of the vacuum in the pleural cavity can lead to a collapse of the lung and thereby can lead to breathing problems and decreased oxygen levels of the patient. The case of a tension pneumothorax constitutes an acute and severe medical condition, wherein the overpressure may quickly lead to hypoxia or even respiratory arrest.

To relieve a tension pneumothorax, a needle thoracostomy, i.e. a puncturing of the thoracic cavity wall with a needle, can be performed to relieve the overpressure within the pleural cavity. However, in most cases a subsequent thoracotomy has to be performed, i.e. a small medical surgery to open the thoracic cavity wall with a scalpel or scissors, which has to be followed by the introduction of a flexible tube into the pleural cavity to reinstate the vacuum. A thoracotomy requires medically trained personnel and surgical equipment, which may not be present at the site of the intervention, for example in the case of blast injury or a ballistic trauma of the thoracic cavity wall in a war zone.

The Chinese patent application CN 2149904 proposes a semi-flexible tube into which a pointed metal core can be inserted to puncture the thoracic cavity wall and insert the semi-flexible tube into the pleural cavity without extensive surgical knowledge. The inner pointed core can subsequently be removed, such that only the semi-flexible tube remains inserted in the pleural cavity. By vacuum pumping through the semi-flexible tube, the pneumothorax can be relieved.

The United States patent application US 2016/0022312 A1 provides another needle assembly for relieving a pneumothorax, wherein a trocar, i.e. a straight hollow needle with a pointed tip, can be used to puncture a thoracic cavity wall, and an inner tube with a blunt end piece is arranged to protrude from the tip of the trocar after puncturing the thoracic cavity wall, such that the risk for damaging the inner organs of the patient, such as the lung or the heart, can be reduced when compared with a trocar without the blunt end piece. Again, by vacuum pumping through the inner tube, an acute pneumothorax can be relieved.

US 2003/0236818 A1 discloses a multi-cannula surgical instrument, which allows the simultaneous in- and outflow of fluids through a lumen, such as to flush an anatomical cavity, the multi-cannula surgical instruments being employable as an electrocautery instrument. The instrument comprises an outer cannula and an inner cannula, wherein the outer cannula is sharp in order to be able to penetrate tissue. The inner cannula can provide a blunt distal tip, such that the multi-cannula can be used as a safety needle. Orifices at the blunt distal end of the inner cannula can be in fluid connection with inner ducts of the inner canula. The inner cannula can be connected to a biasing mechanism, said biasing mechanism allowing retracting and advancing the blunt distal tip during the use of the surgical instrument. The instrument can be adapted to penetrate the tissue of a closed anatomical cavity, such as the pleural space and can have a bent shape.

Following the intervention using any of the above mentioned prior art devices, the patient should be transferred to a surgical facility for further treatment.

SUMMARY OF THE INVENTION

The known methods and corresponding devices for relieving a pneumothorax entail the problem that medically trained personnel is required at the site of the surgical intervention and that using known needle assemblies does not provide the possibility for a direct and secure transport of the patient after the temporary relief. In particular, straight needles entail a risk of puncturing the lung and may slide out of the thoracic cavity during transport or the respiratory act of the patient, while semi-flexible tubes can be pinched by the ribs in the thoracic cavity wall and may therefore provide only a temporary relief.

The object of the invention is therefore to provide a simple means for relieving a pneumothorax, which can be used by non-surgically trained personnel and may prepare the patient for direct transport to a surgical operating room, preferably without a further surgical intervention.

This object is solved by a needle assembly for relieving a pneumothorax according to the independent claims. The dependent claims relate to preferred embodiments. The invention is described with reference to a pneumothorax but can equally be used for relieving an accumulation of liquid in the pleural cavity such as in the case of a hemothorax, a chylothorax or a hydrothorax.

According to a first aspect, the invention relates to a needle assembly for relieving a pneumothorax, the needle assembly comprising a canula. The canula comprises a distal end portion comprising a cutting end for puncturing a thoracic cavity wall, a proximal end portion for removing a fluid or gas from a thoracic cavity, a first curved portion between the distal end portion and the proximal end portion, an intermediate portion between the first curved portion and the proximal end portion, and a first fixing bulge arranged between the first curved portion and the intermediate portion. An outer diameter of the canula at the first fixing bulge is increased with respect to the diameter of the intermediate portion, said first fixing bulge being arranged such as to be placed at or close to the inner surface of the thoracic cavity wall, when the canula is inserted for relieving the pneumothorax, such as to prevent or to reduce the risk that the canula inadvertently slides out of its inserted position.

To bring the needle assembly into the inserted position and relieve the pneumothorax, the thoracic cavity wall is punctured by the cutting end between adjacent ribs. After penetrating the thoracic cavity wall with the cutting end, the canula can be inserted into the pleural cavity and a fluid and/or gas may be removed from the pleural cavity via the lumen of the hollow canula.

During the insertion of the canula into the pleural cavity, the first curved portion of the canula changes the angle of the orientation of the distal end portion with respect to the thoracic cavity wall, such that the distal end portion can be guided on a curved trajectory away from the lung or the heart. After the first curved portion passes the thoracic cavity wall, the canula acquires the inserted position such that the distal end portion with the cutting end may lie close to the thoracic cavity wall, the inserted position being associated with a reduced risk of inadvertent injury of internal organs.

Thus, the possibility for puncturing the lung or the heart with the cutting end during a movement of the thoracic cavity wall and/or the lung due to the respiratory act of the patient may be reduced as compared to the case where a straight needle or canula is used. As the canula is guided into the inserted position by the first curved portion, the first curved portion may reduce the required surgical skill during the intervention. In the inserted position, the curvature of the first curved portion may also reduce the risk that the canula inadvertently slides out of its inserted position.

The intermediate portion may at least partially reside within the thoracic cavity wall in the inserted position of the canula. Additionally, the needle assembly comprises the first fixing bulge arranged between the first curved portion and the intermediate portion, such that the first fixing bulge may abut against the inner surface of the thoracic cavity wall in the inserted position of the canula. The first fixing bulge provides a resist against the canula sliding out of the pleural cavity, and may therefore improve the stability of the needle assembly in the inserted position during a subsequent transport of the patient. The intermediate portion preferably has a low curvature, and in particular is substantially straight, to reduce any strain caused by unintended movement of the canula in the inserted position to the surrounding tissue and/or to minimize displacement and/or orientation change of the cutting end caused by unintended movement.

The proximal end portion may be fitted with suitable means for relieving the pneumothorax, such as valves, standardized adapters for connecting a suction tube to the canula, or the like. Hence, by applying a vacuum pressure to the proximal end portion of the canula, the acute pneumothorax may be relieved and the vacuum within the pleural cavity may be at least partially reinstated. When the vacuum is reinstated, the first curved portion allows a non-perpendicular orientation of the cutting end to the visceral pleura or parenchyma of the inflated lung. The first fixing bulge increases the stability of the inserted position of the canula and thereby further reduces the risk of injury.

In preferred embodiments, the outer diameter of the first fixing bulge exceeds the diameter of the intermediate portion by at least 10% of the diameter of the intermediate portion, in particular by at least 20% of the diameter of the intermediate portion, and preferably by between 20% and 50% of the diameter of the intermediate portion.

An increase of the outer diameter of the first fixing bulge compared to the outer diameter of the intermediate portion of at least 10%, preferably of at least 20%, may sufficiently fix the relative position of the canula with respect to the thoracic cavity wall during a transport of the patient. An outer diameter of the first fixing bulge of at most 50% of the diameter of the intermediate portion may reduce the damage to the tissue of the thoracic cavity wall due to the insertion, and/or facilitate the contraction of the tissue of the thoracic cavity wall around the intermediate portion after inserting the canula, such that a tight seal and/or fixed position may be achieved.

In preferred embodiments, an angle between the orientation of the distal end portion and the orientation of the intermediate portion is between 30° and 120°, in particular between 60° and 120°, preferably between 70° and 110°.

The orientations of the respective portions of the canula are defined by the axial direction of the canula in the respective portion. The optimal angle between the orientation of the distal end portion and the orientation of intermediate portion may depend on the position where the thoracic cavity wall is to be punctured. In some embodiments, the angle is substantially 90°, such that the distal end portion lies substantially parallel with respect to the thoracic cavity wall in the inserted position of the canula, such that the chances for injuring the inner organs or inner surface of the thoracic cavity wall are minimized, when the vacuum in the pleural cavity is reinstated.

In preferred embodiments, the cutting end comprises a bevel arranged at the distal end of the distal end portion, in particular a bevel with a pointed tip.

A canula with a bevel as the cutting end may be easily produced, while an intake diameter of the canula may be unaffected by the cutting end, such that a risk of clogging the distal end portion may be low. The pointed tip may improve the cutting action of the cutting end and may hence allow an easier insertion of the canula into the pleural cavity.

In some embodiments, the bevel further comprises a slanted portion, such that a radially inward portion of the beveled cutting end protrudes further from the distal end portion than a radially outward portion of the beveled cutting end. Hence, the sharpest point of the bevel, i.e. the cutting edge, may be located at a radially inward position. With the cutting edge located at the radially inward position, the risk of inadvertent injury in the inserted position by the lateral portions of the cutting end may be reduced.

In preferred embodiments, the bevel tip is located on a cylindrical surface defined by the distal end portion of the canula at an angular position chosen such that the bevel tip is closest to the thoracic cavity wall when the canula is inserted for relieving a pneumothorax, or at an angular position that deviates from said angular position by 90° or less, in particular by 60° or less, and preferably by 45° or less.

The cylindrical surface can be defined by a virtual cylindrical extension of the distal end portion in the distal direction. The bevel tip corresponds to the point of the distal end portion protruding the farthest in the distal direction. The angular position of the bevel tip is defined by the relative position of the bevel tip on the cylindrical surface with respect to the central axis of the cylindrical surface, when the distal end portion is viewed along the axial direction of the canula.

When the bevel tip is in the angular position closest to the thoracic cavity wall when the canula is inserted for relieving a pneumothorax, referred to as the proximal angular position, the risk of cutting the visceral pleura of the re-inflated lung may be minimized.

Further, said proximal angular position may reduce the risk of damaging the inner organs during the insertion of the canula into the pleural cavity. During the insertion of the canula into the inserted position, the cutting end is first oriented perpendicular with respect to the sidewall of the lung and subsequently follows a curved trajectory imposed by the first curved portion of the canula. When the bevel tip is arranged in said proximal angular position, then the tip is oriented at an angular position in the direction of curvature during the curved trajectory. In this way, the bevel tip may be further away from the organs of the patient while on the curved trajectory and the risk of injury may thereby be decreased.

It is possible to deviate from said proximal angular position closest to the thoracic cavity wall to reduce a risk of injury to the thoracic cavity wall by the cutting end, when the canula is in its inserted position. Depending on the shape of the tip it may therefore be possible, and in some cases advantageous to deviate from said angular position, for example by an angle between 30° and 90°, such that the bevel tip is arranged laterally in the inserted position to reduce the risk of unintended tissue damage to the parietal pleura of the thoracic cavity wall.

In preferred embodiments, the distance between the tip of the distal end portion and the first curved portion of the canula is greater than 2.5 cm, in particular greater than 3 cm, and preferably between 3 cm and 6 cm.

Preferably, the distance between the tip of the distal end portion and the first curved portion is greater than the average thickness of the muscular tissue around the ribs of the thoracic cavity wall. In this way, a substantially straight insertion path with a low curvature may be provided, and the cutting end may follow the curved trajectory only once the distal end portion has punctured the thoracic cavity wall. The average thickness of the thoracic cavity wall may correspond to a distance between 1.5 cm and 3 cm. By choosing a distance between the tip of distal end portion and the first curved portion greater than 2.5 cm or 3 cm, a tolerance range for different patients with varying size and/or body composition may be provided. The distance between the tip of the distal end portion and the first curved portion also defines the insertion depth into the pleural cavity and may be smaller than 6 cm to reduce the risk of damaging internal organs during the insertion of the canula.

In preferred embodiments, a minimal diameter of the canula is greater than 2 mm, in particular greater than 3 mm, and preferably between 3 mm and 8 mm.

Generally, the diameter of the canula may be chosen to be smaller than the distance between ribs, with smaller diameters reducing the tissue damage caused by the insertion of the canula and/or facilitating the insertion of the canula. A minimal diameter greater than 2 mm may guarantee a sufficient flow rate through the canula to remove gas and/or liquids from the pleural cavity and may reduce the risk of clogging the canula. The choice of a greater minimal diameter such as 3 mm may reduce the complexity of fabricating and/or modifying the canula and further increases the possible flow rate through the canula.

In preferred embodiments, the needle assembly comprises a blunt end piece, which is movable between a protruding position, in which the blunt end piece extends in a distal direction beyond the cutting end, and a retracted position, in which the blunt end piece is retracted behind the cutting end such as to expose the cutting end for a puncturing operation, and an elastic element for biasing said blunt end piece towards the protruding position. In preferred embodiments, the elastic element is a spring. A spring constant of the elastic element is preferably greater than 0.5 N/cm, and most preferably greater than 2 N/cm.

In the protruding position the blunt end piece can prevent an inadvertent injury of an internal organ or body tissue by the cutting end. The elastic element allows changing between the protruding and the retracted position, and thereby allows bringing the blunt end piece into the retracted position for puncturing the thoracic cavity wall. After the penetration of the thoracic cavity wall, the blunt end piece may protrude beyond the cutting end and may thereby prevent the cutting end from inadvertently cutting the parietal or visceral pleura delimiting the pleural cavity.

Due to the biasing force of the elastic element, the blunt end piece acquires the protruding position when no additional external force is applied to the blunt end piece which exceeds the bias of the elastic element. The blunt end piece may automatically be retracted by an axial resisting force occurring during the puncturing of the thoracic cavity wall and subsequently be moved automatically into the protruding position by the biasing force, when the cutting end enters the pleural cavity and the resisting force vanishes.

The biasing strength of the elastic element should be chosen such that the force necessary to puncture the thoracic cavity wall is sufficient to bring the blunt end piece into the retracted position. At the same time, the bias should be selected high enough such that the blunt end piece reliably acquires the protruding position, i.e. protrudes beyond the cutting end after puncturing the thoracic cavity wall.

In some embodiments, the blunt end piece is arranged at least partially inside the canula, and is in particular arranged to retract further into the canula when the blunt end piece is moved between the protruding and the retracted position.

In some embodiments, the elastic element connects the blunt end piece to the proximal end portion, e.g. by a flexible hollow tube disposed within the canula, such that the position of the blunt end piece may be varied or monitored by the operator during the intervention.

In some embodiments, the blunt end piece is arranged outside the canula, such as to prevent or to reduce a cutting action of the cutting end in a lateral or radial direction when the blunt end piece protrudes in the protruding position, and is in particular arranged circumferentially around the distal end portion of the canula, wherein the blunt end piece preferably comprises a hollow cylinder shaped portion, such as to at least partially enclose the distal end portion in a radial direction of the canula. Most preferably, the blunt end piece is arranged substantially concentric with the distal end portion.

When the blunt end piece is arranged inside the canula, the effective diameter of the distal end portion of the canula may not be enlarged by the blunt end piece, and hence, the incision caused by inserting the canula into the inserted position may have a small diameter leading to lower tissue damage originating from the insertion of the canula. When the blunt end piece is arranged outside the canula, the lateral cutting action of the cutting end may be minimized when the distal end portion has penetrated the thoracic cavity wall and the canula is inserted into the pleural cavity. A transport of the patient may then be associated with a lower risk of tissue damage.

In preferred embodiments, the canula further comprises a second curved portion arranged between the first curved portion and the distal end portion, the second curved portion having a lower curvature than the first curved portion, wherein the curvature of the second curved portion is preferably in the same plane and in the same direction as the curvature of the first curved portion.

The second curved portion may favorably define the trajectory of the cutting end in the pleural cavity during the insertion of the canula into the inserted position. As the curvature is in the same plane and in the same direction as the curvature of the first curved portion, the trajectory of the cutting end during the insertion of the canula into the pleural cavity may be closer to the thoracic cavity wall than a trajectory established with a straight portion. Thus, the risk of injuring the inner internal organs lying further away from the thoracic cavity wall of the patient may be reduced by the second curved portion. Additionally, the second curved portion may reduce the incidence angle between the cutting end and the lung during the insertion of the canula, and may thereby further reduce the risk of injury to the patient.

In preferred embodiments, the canula and/or the blunt end piece further comprises a lateral opening close to the cutting end for removing a fluid and/or gas from the thoracic cavity, in particular an opening with a rounded contour, and preferably an oval opening.

The lateral opening close to the cutting end may allow the removal of fluid and/or gas from the pleural cavity and is less prone to clogging by body tissue and/or fluids than an opening at the front of the distal end portion. A rounded contour of the opening may reduce a risk of tissue damage caused by the rim of the lateral opening. In some embodiments, the canula and the blunt end piece comprise corresponding openings and/or slots arranged to provide a common path for removing a fluid and/or gas from the thoracic cavity.

The needle assembly may also comprise means to inhibit the canula from sliding further into the pleural cavity from its inserted position.

In preferred embodiments, the canula comprises a second fixing bulge arranged between the intermediate portion and the proximal end portion. An outer diameter of the canula is increased at the second fixing bulge and said second fixing bulge is arranged such as to be placed at or close to the outer surface of the thoracic cavity wall, when the canula is inserted for relieving the pneumothorax, such as to prevent or to reduce the risk that the canula inadvertently slides into the thoracic cavity. Preferably, the outer diameter of the second fixing bulge exceeds the diameter of the intermediate portion by at least 10% of the diameter of the intermediate portion, and more preferably by at least 20% of the diameter of the intermediate portion.

As the second fixing bulge may be arranged to be placed at or close to the outer surface of thoracic cavity wall, a resist against the canula sliding further into the pleural cavity can be provided.

In preferred embodiments, a length of the intermediate portion is greater than 2 cm, in particular greater than 3 cm, and preferably smaller than 4.5 cm.

When the length of the intermediate portion is greater than 2 cm, the distance between the first fixing bulge and the second fixing bulge may be greater than the thickness of the thoracic cavity wall of an average patient. Hence, the intermediate portion may acquire a fixed position within the thoracic cavity wall and the first and second fixing bulges may inhibit or restrict movement of the canula with respect to the thoracic cavity wall. The length of the intermediate portion may be chosen depending on the expected thickness of the thoracic cavity wall of the patient, e.g. a greater length of the intermediate portion may be chosen when the patient has thicker muscular tissue.

In preferred embodiments, the needle assembly further comprises a fixing plate arranged on the canula and close to the proximal end portion. The fixing plate is arranged to abut on the outer surface of a patient's chest when the canula is inserted for relieving the pneumothorax. The fixing plate is further suitable for fixing the position of the needle assembly with respect to the thoracic cavity wall.

The fixing plate may be arranged to be movable along the canula, such as to adapt the position of the fixing plate to the thickness of the patient's thoracic cavity wall. For fixing the position of the needle assembly relative to the thoracic cavity wall, the fixing plate may comprise a supporting surface spaced radially apart from the canula to abut on the outer surface of the patient's chest and for fixing the position of the needle assembly using a tape.

In some embodiments, the fixing plate is arranged on the second fixing bulge.

In preferred embodiments, the canula is made of surgical steel.

A canula made of surgical steel may provide a limited flexibility for performing an accurate intervention while at the same time providing sufficient rigidity to not be pinched and/or deformed by the respiratory action of the patient, and to define the position of the cutting end in the inserted position of the canula by the shape of the canula. Further, surgical steel may be easily sterilized prior to use.

In preferred embodiments, the needle assembly further comprises a pressure relief valve connected or connectable to the proximal end portion of the canula.

The pressure relief valve may allow automatically relieving a tension pneumothorax upon insertion of the canula into the pleural cavity, while unintended entry of air into the pleural cavity via the canula may be inhibited.

In a second aspect the invention relates to a needle assembly for relieving a pneumothorax, the needle assembly comprising a canula. The canula comprises a distal end portion comprising a cutting end for puncturing a thoracic cavity wall, a proximal end portion for removing a fluid or gas from a thoracic cavity and a first curved portion between the distal end portion and the proximal end portion. The needle assembly further comprises a blunt end piece, which is movable between a protruding position, in which the blunt end piece extends in a distal direction beyond the cutting end, and a retracted position, in which the blunt end piece is retracted behind the cutting end such as to expose the cutting end for a puncturing operation. The needle assembly further comprises an elastic element for biasing said blunt end piece towards the protruding position. The elastic element is preferably a spring. A spring constant of the elastic element is preferably greater than 0.5 N/cm, and most preferably greater than 2 N/cm.

In preferred embodiments, the needle assembly according to the second aspect comprises any combination of the properties or features of the needle assemblies according to the first aspect described above.

DETAILED DESCRIPTION OF EMBODIMENTS

The features and numerous advantages of the needle assembly according to the present invention will best be understood from a detailed description of preferred embodiments with reference to the accompanying drawings, in which.

Figure 1:
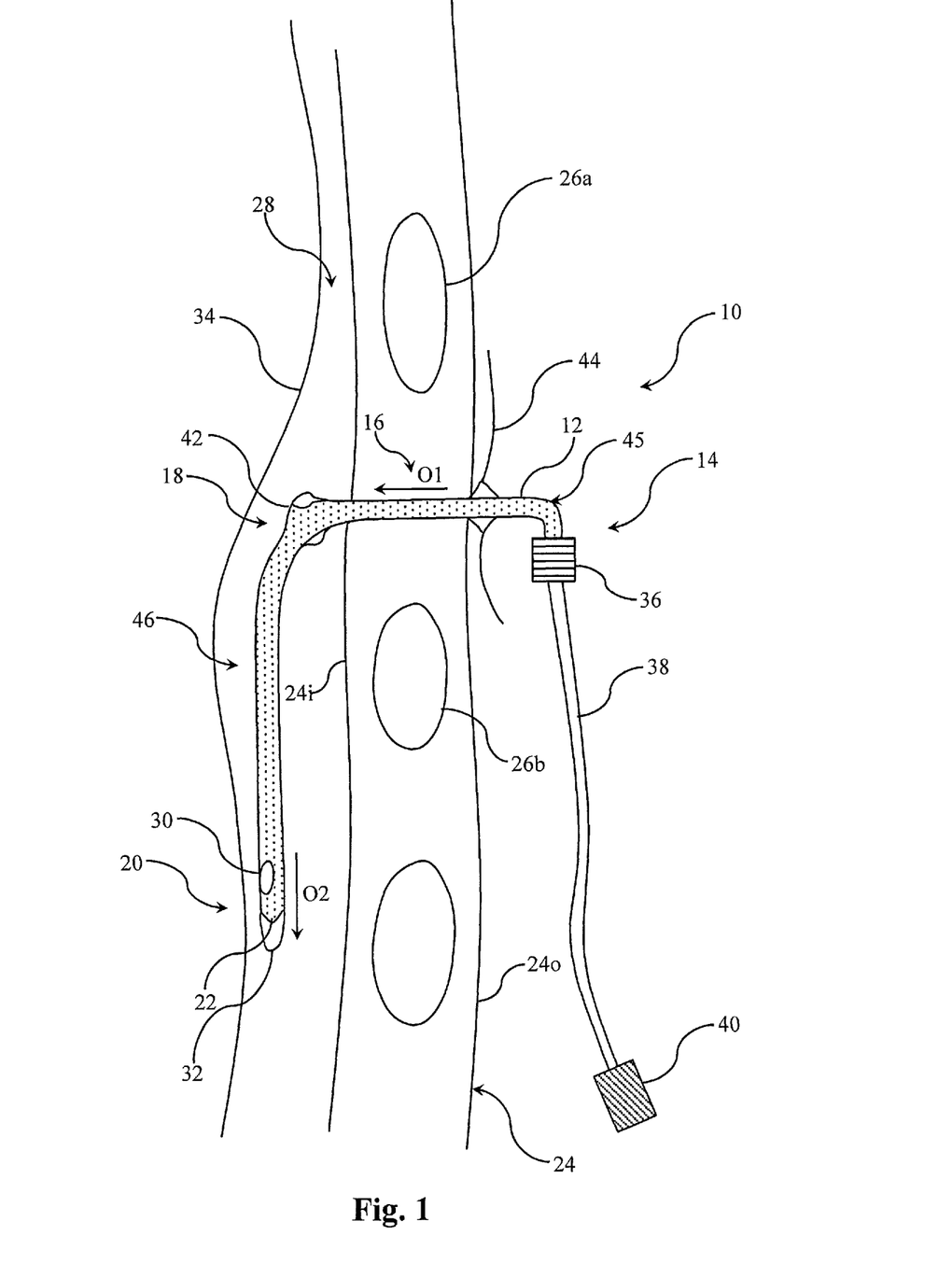
FIG. 1 is a schematic illustration of a needle assembly in the inserted position according to an example.

FIG. 1 shows a needle assembly 10 in its inserted position for relieving a pneumothorax. The needle assembly 10 comprises a canula 12 with a proximal end portion 14, an intermediate portion 16, a first curved portion 18, and a distal end portion 20 with a cutting end 22. In the inserted position shown in FIG. 1, the intermediate portion 16 resides within the thoracic cavity wall 24 between adjacent ribs 26a, 26b.

The distal end portion 20 lies within the pleural cavity 28 and comprises a lateral opening 30 for removing a gas and/or liquid from the pleural cavity 28 and thereby reinstating the vacuum in the pleural cavity 28 in case of a pneumothorax. The distal end portion 20 also accommodates a blunt end piece 32, which in the illustration of FIG. 1 protrudes from the cutting end 22. The blunt end piece 32 may reduce the risk of the cutting end 22 injuring the inner tissue of the patient, such as the lung 34, when the canula 12 is in its inserted position.

For removing gas and/or a liquid from the pleural cavity 28, the proximal end portion 14 comprises an adapter 36 connected by a flexible tube 38 to the pressure relief valve 40. The adapter 34 may allow connecting the canula 12 to any further instrumentation for relieving the pneumothorax and may for example correspond to a Luer-lock compatible termination. In other embodiments, the relief valve 40 may be directly connected or connectable to the proximal end portion 14 or to the adapter 36.

The canula 12 can provide a path for the gas and/or liquid to leave the pleural cavity 28. By applying a vacuum pressure to the pressure relief valve 40 of FIG. 1, such as by a suitable pump, the pneumothorax can be relieved. The pressure relief valve 40 may further allow automatically relieving a tension pneumothorax upon insertion of the canula 12 into the pleural cavity 28, while it may prevent entry of outside air into the pleural cavity 28.

For fixing the canula 12 in its inserted position and thereby fixing the relative position of the needle assembly 10 with respect to the thoracic cavity wall 24, the needle assembly 10 comprises a first fixing bulge 42 located close to the inner surface 24i of the thoracic cavity wall 24 when the canula 12 is in its inserted position. The first fixing bulge 42 features an outer diameter D2 exceeding the outer diameter D1 of the canula 12 in the intermediate portion 16 and thereby reduces the risk for the canula 12 to slide out from the pleural cavity 28 (further illustrated in FIG. 6).

For preventing the canula 12 from sliding further into the pleural cavity 28, the displayed needle assembly 10 comprises a fixing plate 44 arranged to abut against the outer surface 24o of the thoracic cavity wall 24. The fixing plate 44 may be movable along the canula 12 to allow for adapting the needle assembly 10 to differences of the thickness of the thoracic cavity wall 24 between patients. The movement of the fixing plate 44 may be limited along the canula 12 in the proximal direction by a further curved portion 45 (as shown in FIG. 1) or by a further bulge (not shown) between the proximal end portion 14 and the intermediate portion 16 to indicate the maximal insertion depth to a surgically unskilled operator.

The curved portion 18 changes the orientation O1 of the intermediate portion 16 with respect to the orientation O2 of the distal end portion 20, the orientations O1, O2 being defined by the axial direction of the canula 12 in the respective portions 16, 20. In FIG. 1, the orientations O1, O2 form an angle of substantially 90°, such that the orientation O2 of the distal end portion 20 may be substantially parallel to the inner surface 24i of the thoracic cavity wall 24 in the inserted position.

Figure 2:
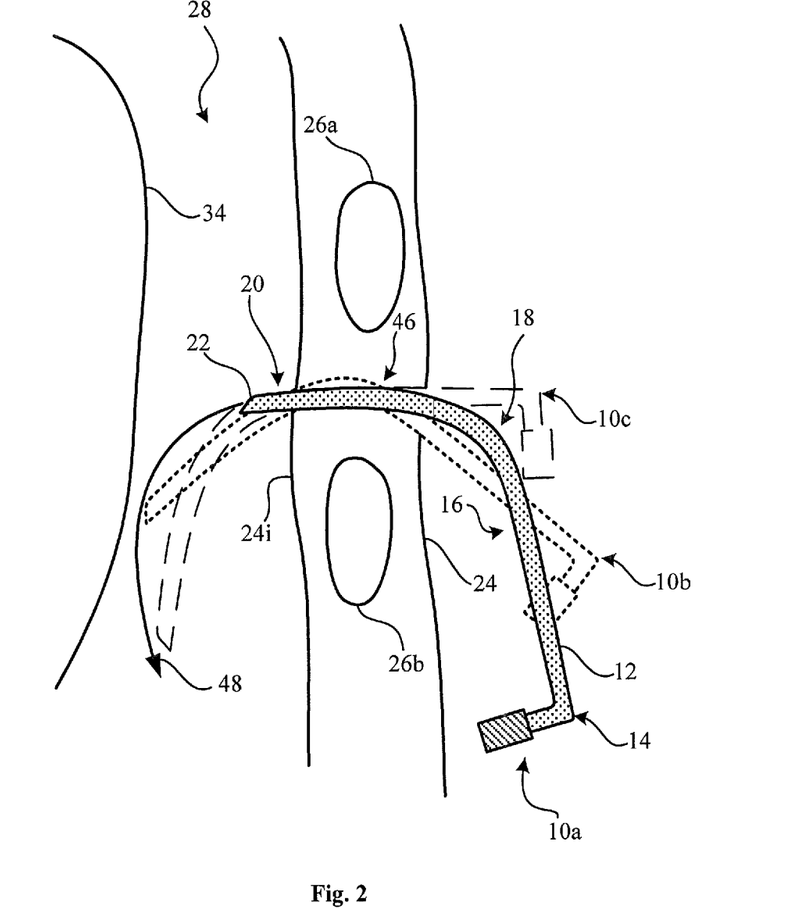
FIG. 2 is a schematic illustration of an insertion path of an exemplary canula according to an example.

The canula 12 shown in FIG. 1 also comprises a second curved portion 46, which is curved in in the same plane and the same direction as the first curved portion 18, but has a lower curvature than the first curved portion 18. As shown in FIG. 2, the curved portions 18, 46 may guide the cutting end 22 along a curved trajectory 48 of the canula 12 during the insertion of the canula 12 into the pleural cavity 28 of the patient. After following the curved trajectory 48, the distal end portion 20 may lie close to the thoracic cavity wall 24 in the inserted position and, as shown in FIG. 1, may be substantially parallel to the thoracic cavity wall 24. Hence, the tip of the cutting end 22 can be oriented substantially parallel to the surface of the lung 34, the heart of the patient (not shown) or the thoracic cavity wall 24, and the risk for inadvertently injuring the patient may be reduced as compared to a straight canula.

In particular, since in the needle assembly 10 the distal end portion 20 lies close to the thoracic cavity wall 24 in the inserted position, the patient may be prepared for immediate transport to an operating room after the insertion. Further, the surgical skill required for relieving a pneumothorax with the needle assembly 10 may be reduced, since the inserted position may be acquired automatically by the canula 12 during the insertion into the pleural cavity 28 due to the curved trajectory 48 imposed by the first curved portion 18, and since the protruding blunt end piece 32 can limit the unintentional damage to the body tissue coming into contact with the cutting edge 22.

The intervention with the needle assembly 10 is illustrated in FIG. 2 where the exemplary curved trajectory 48 is shown. FIG. 2 shows a first needle assembly position 10a, a second needle assembly position 10b and a third needle assembly position 10c during different stages of the insertion of the canula 12 into the pleural cavity 28.

In the first needle assembly position 10a, the cutting end 22 has just penetrated the thoracic cavity wall 24 between adjacent ribs 26a, 26b and protrudes into the pleural cavity 28. The cutting end 22 may puncture the thoracic cavity wall 24 in any suitable position, such as the between the fifth and sixth rib below the armpit of the patient (i.e. the Bülau position) or between the second and third rib below the middle of the clavicle (i.e. the Monaldi position).

In the second needle assembly position 10b, the first curved portion 18 is partially located within the thoracic cavity wall 24, and hence, the cutting end 22 of the canula 12 is guided along a curved trajectory 48 and thereby changes the angle between the orientation of the cutting end 22 and the normal direction of the inner surface 24i of the thoracic cavity wall 24. By using a needle assembly 10 with a second curved portion 46 between the first curved portion 18 and the distal end portion 20, a curvature of the curved trajectory 48 may be smoothed, which may lead to reduced damage to the tissue of the thoracic cavity wall 24 and to a reduced distance between the cutting end 22 and the inner surface 24*i* of the thoracic cavity wall 24 during the insertion of the canula 12.

In the third needle assembly position 10*c*, the first curved portion 18 has passed the thoracic cavity wall 24, and hence, the cutting end 22 of the canula 12 is oriented substantially parallel with respect to the inner surface 24*i* of the thoracic cavity wall 24. Thus, the risk of puncturing or cutting the sidewall of the re-inflated lung 34 with the cutting end 22 during the respiratory act of the patient or during vibrations originating from a transport of the patient may be minimized.

For puncturing the thoracic cavity wall 24 and removing gas and/or fluids from the pleural cavity 28, the minimal outer diameter of the canula 12 may be greater than 2 mm, such as 3 mm.

For reducing the risk of puncturing inner organs, such as the lung 34, with the cutting end 22 during the insertion of the canula 12 or for reducing the occupied space of the canula 12 in the pleural cavity 28 in the inserted position, the length of the canula 12 between the tip 50 of the cutting end 22 and the first curved portion 18 may be smaller than 6 cm. Further, said length should preferably be larger than 2 cm, such that a straight or only moderately curved portion of the canula 12 for puncturing the thoracic cavity wall 24 may be provided.

The exemplary needle assembly 10 may therefore allow a surgically unskilled operator to relieve a pneumothorax in one step, with the insertion of the canula 12 requiring only one hand for the intervention. The shape of the canula 12 may automatically bring the cutting end 22 into the inserted position illustrated in FIG. 1 after penetrating the thoracic cavity wall 24, such that a risk of damage to the parietal and/or visceral pleura after the reinstatement of the vacuum in the pleural cavity 28 may be minimized.

Figure 3:
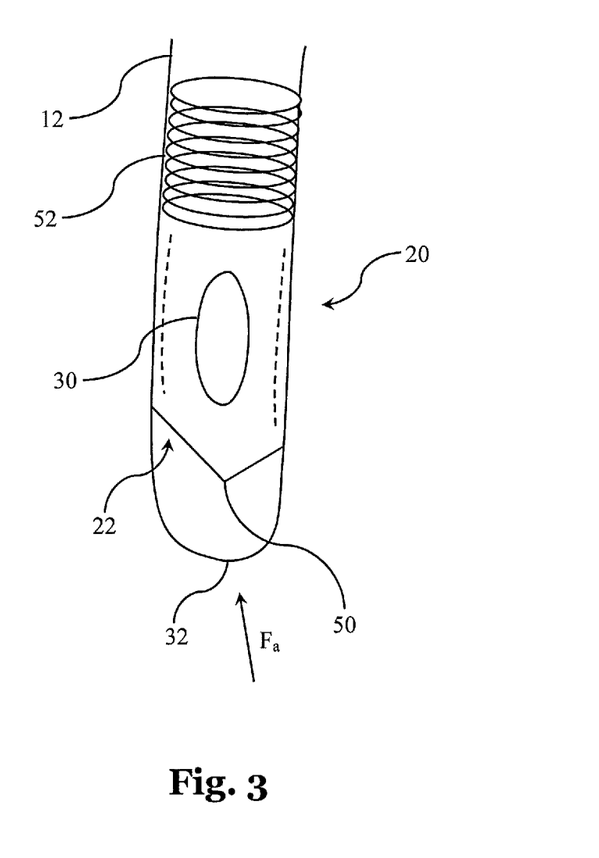
FIG. 3 is a schematic illustration of a distal end portion of a needle assembly according to an example.

The distal end portion 20 of an exemplary canula 12 is illustrated in more detail in FIG. 3. The distal end portion 20 comprises a beveled cutting end 22 with a pointed tip 50 to puncture the thoracic cavity wall 24. A lateral opening is arranged close to the cutting end 22 for removing gas and/or a liquid from the pleural cavity 28.

Figure 4A:
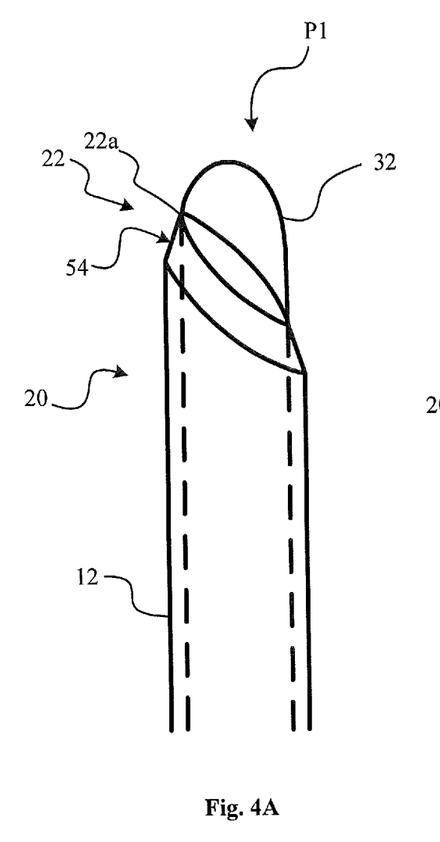
FIG. 4A is a schematic illustration of a beveled cutting end with a blunt end piece in a protruding position according to an example.
Figure 4B:
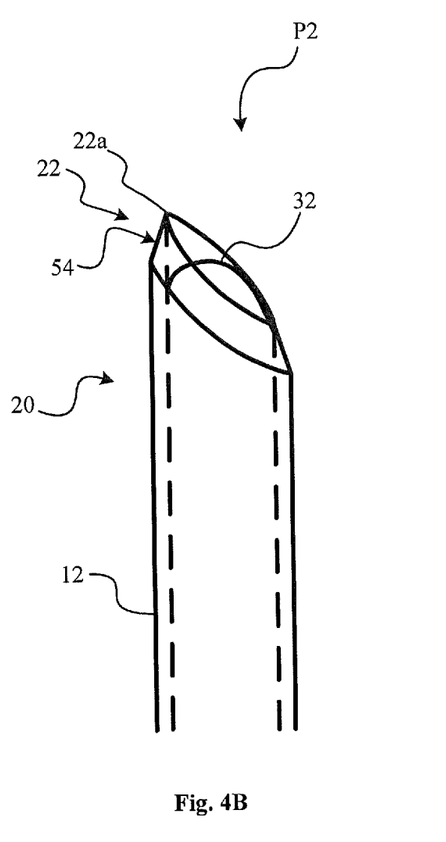
FIG. 4B is a schematic illustration of a beveled cutting end with a blunt end piece in a retracted position according to an example.

To reduce the risk of further tissue damage after the insertion of the canula 12, the illustrated distal end portion 20 accommodates the blunt end piece 32, which is movable between a protruding position P1 (as in FIG. 3) and a retracted position P2 (not shown in FIG. 3, but illustrated in the example of FIG. 4B). The blunt end piece 32 is biased by a spring 52, such that the blunt end piece 32 protrudes beyond the pointed tip 50 of the cutting end 22 as long as an axial force $F_a$ onto the blunt end piece 32 remains smaller than a predefined threshold. The threshold is defined by the spring constant of the spring 52.

Preferably, the spring constant is chosen such that, when the necessary force to puncture the thoracic cavity wall 24 with the cutting end 22 is applied along the axial force direction $F_a$ onto the blunt end piece 32, the blunt end piece 32 is retracted behind the cutting end 22 into the retracted position P2. In the retracted position P2, the beveled cutting end 22 may cleanly puncture the thoracic cavity wall 24 such that the tissue damage by the intervention may be minimized. For example, the spring constant may be 2 N/cm to define a suitable threshold for a distal end portion with an outer diameter of 3 mm and a beveled cutting end 22.

After penetrating the thoracic cavity wall 24, the spring 52 moves the blunt end piece 32 into its protruding position P1, such that the risk for inadvertently cutting body tissue with the cutting end 22 is minimized in the inserted position of the canula 12. The spring 52 may be accommodated in the canula 12 between the cutting end 22 and the first curved portion 18 as shown in FIG. 3 for limiting the friction of the blunt end piece 32 in the canula 12 due to any of the curved portions 18, 46. However, the spring 52 may also be arranged close to the proximal end portion 14 of the canula 12 to allow monitoring or influencing the position of the blunt end piece 32 by the operator. For example, the blunt end piece 32 may be connected to a hollow flexible tube arranged in the canula 12 between the distal end portion 20 and the proximal end portion 14 for removing fluids and/or gas from the pleural cavity 28 and/or monitoring or influencing the position of the blunt end piece 32 at the proximal end portion 14.

In FIG. 3, the lateral opening is shown as being located between the tip of the blunt end piece 32 and the spring 52. By arranging the lateral opening 30 in a position close to the tip 50 of the canula 12, a removal of liquid from the pleural cavity 28 may be improved as compared to a position closer to the first curved portion 18. To provide a path for a gas and/or liquid through the lateral opening 30, when the lateral opening 30 is arranged in the position close to the tip 50 of the canula 12, the blunt end piece 32 may be at least partially hollow and comprise slots and/or openings (not shown) associated with the lateral opening 30, such that a connection may be established between the pleural cavity 28 and the proximal end portion 14 through the canula 12 in the inserted position of the canula 12.

However, the lateral opening 30 does not have to be arranged between the spring 52 and the blunt end piece 32 and may be arranged anywhere along the needle assembly 10 as long as the connection between the pleural cavity 28 and the proximal end portion 14 through the canula 12 may be established, and may for example be arranged anywhere between the tip 50 and the first curved portion 18 or on a lateral side of the blunt end piece 32. In some embodiments, an opening for removing fluids and/or gas from the pleural cavity 28 may be an axial opening and may be arranged at the tip of the blunt end piece 32.

The protruding position P1 and the retracted position P2 of the blunt end piece 32 are further illustrated in FIGS. 4A and 4B. FIG. 4A shows the distal end portion 20 of the canula 12 accommodating a blunt end piece 32 in the protruding position P1.

The cutting end 22 in FIG. 4A is beveled to improve a cutting action of the cutting end 22 and further comprises a slanted portion 54, such that a radially inward lying cutting edge 22*a* of the cutting end 22 protrudes further in the distal direction than a radially outward lying portion of the cutting end 22. Due to the slanted portion 54, the cutting edge 22*a* of the cutting end 22 may abut on the blunt end piece 32 in the protruding position P1, such that a cutting action of the cutting end 22 is minimized.

FIG. 4B illustrates the retracted position P2 of the blunt end piece 32, wherein the blunt end piece 32 is retracted behind the cutting end 22 and the cutting edge 22*a* of the cutting end 22 is exposed for puncturing the thoracic cavity wall 24.

Figure 4C:
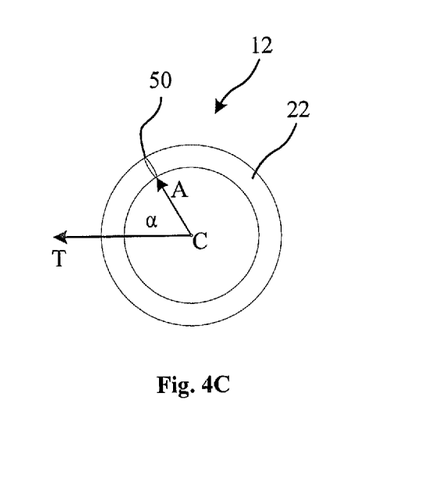
FIG. 4C is a schematic illustration of the distal end portion viewed along an axial direction of the canula illustrating the position of the tip according to an example.

FIG. 4C illustrates the definition of an angular position A for the tip 50. In FIG. 4C, the projection of the cylindrical surface defined by the cutting end 22 is viewed along an axial direction of the distal end portion 20 of the canula 12. The angular position A is defined by the arrow pointing from the central axis C of the canula 12 to the position of the tip 50. A cavity wall direction T defines the direction of the thoracic cavity wall 24 with respect to the position of the central axis C when the canula 12 resides in the inserted position (as shown in FIG. 1). An angle α describing the angular position A of the tip 50 in the inserted position can then be defined between the cavity wall direction T and the angular position A.

When the angle α is chosen to be substantially zero, the tip 50 can be oriented farthest away from the visceral pleura of the lung 34 in the inserted position. By choosing an angle α between 30° and 90°, the tip 50 can be oriented farther away from the parietal pleura of the thoracic cavity wall 24. Hence, by varying the angle α, a compromise for the risk of damaging the visceral and parietal pleura may be chosen.

Figure 5A:
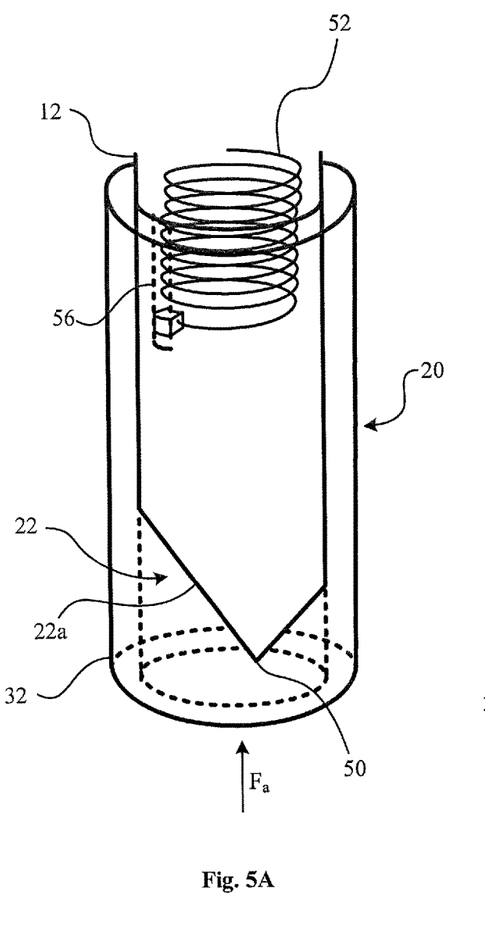
FIG. 5A is a schematic illustration of a distal end portion of a canula with a blunt end piece in the protruding position according to an example.

FIG. 5A shows another view of the distal end portion 20 of the canula 12 according to an example. Instead of arranging the blunt end piece 32 inside the canula 12 as shown in FIGS. 3 and 4, in FIG. 5 the blunt end piece 32 is arranged outside the canula 12 in a radially outward position and in a concentric configuration with the distal end portion 20 of the canula 12. As shown in FIG. 5, the blunt end piece 32 may comprise a hollow cylindrical portion arranged to enclose the distal end portion 20 of the canula 12 in the radial direction and thereby prevent or limit a direct contact between the lateral side of the cutting edge 22a and the parietal or visceral pleura of the patient, when the blunt end piece 32 is in the protruding position P1.

To provide a biasing force for the blunt end piece 32, the blunt end piece 32 may be connected to an elastic element, such as a spring 52 inside or outside the canula 12 to change between a protruding and a retracted position P1, P2. In FIG. 5A, the spring 52 is arranged inside the canula 12, and the blunt end piece 32 is connected to the spring 52 via a slot 56 of the canula 12, such that the blunt end piece 32 is movable, for example within the limits defined by the slot 56, between the protruding position P1 illustrated in FIG. 5A and a retracted position P2 (not shown), which exposes the tip 50 of the cutting edge 22a to puncture the thoracic cavity wall 24.

By arranging the blunt end piece 32 outside the canula 12, the cutting action of the cutting edge 22a in the lateral or radial direction may be minimized, when the blunt end piece 32 is in the protruding position P1.

Figure 5B:
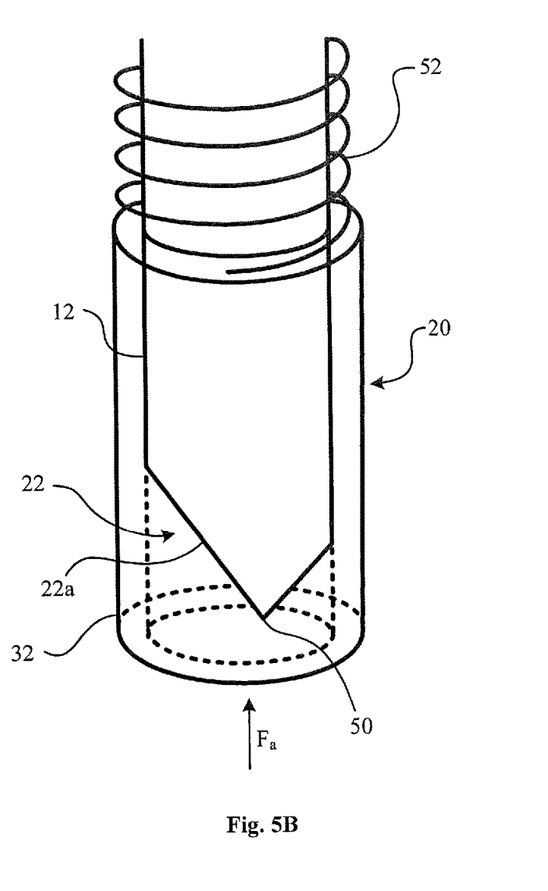
FIG. 5B is a schematic illustration of a distal end portion of a canula with a blunt end piece in the protruding position according to another example.

FIG. 5B shows another example of the distal end portion 20 of a canula 12, wherein the spring 52 movably connects the blunt end piece 32 to the canula 12 and is arranged outside the canula 12 in a concentric configuration with the canula 12.

Arranging the spring 52 outside the canula 12 may reduce a complexity of fabricating the needle assembly 10 compared with an arrangement of the spring 52 within the canula 12. Arranging the spring 52 inside the canula 12 may minimize a risk of pinching or rupturing body tissue with the spring 52.

Figure 6:
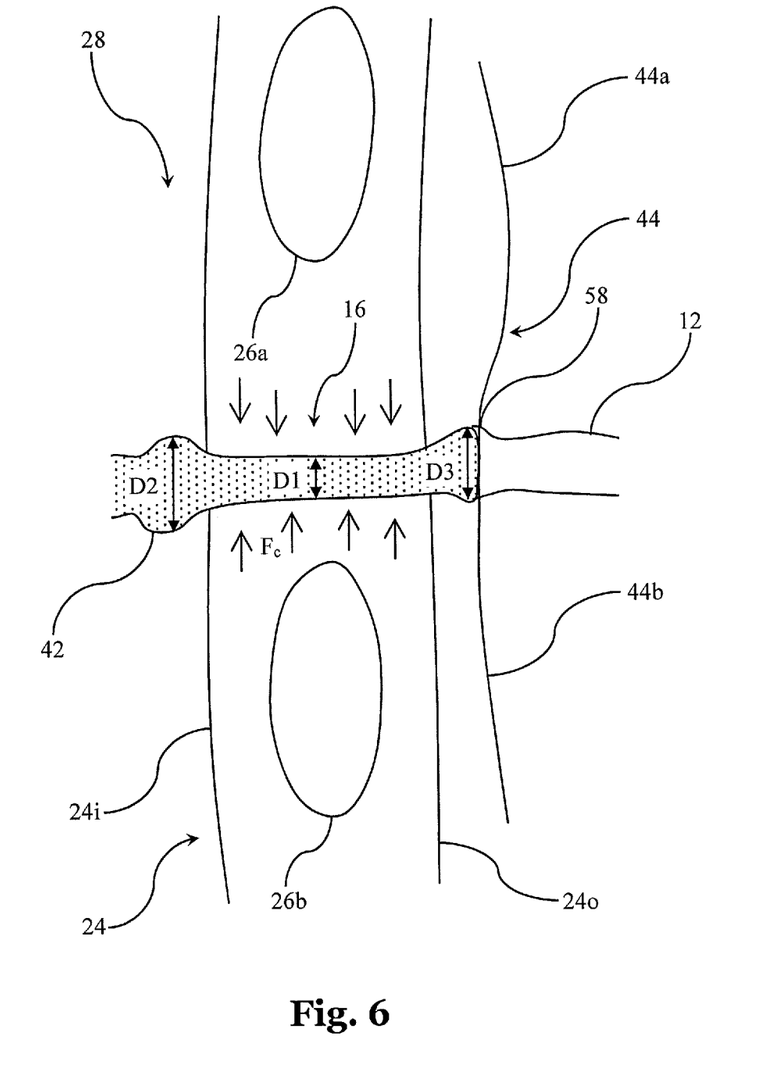
FIG. 6 is a schematic illustration of the portion of a canula lying close to the thoracic cavity wall according to an example.

FIG. 6 shows an exemplary canula 12 in its inserted position with the intermediate portion 16 lying in the thoracic cavity wall 24 between adjacent ribs 26a, 26b. After the insertion of the canula 12, a compressive resetting force $F_c$ of the tissue of the thoracic cavity wall 24 may seal the connection between the inner surface 24i and the outer surface 24o the thoracic cavity wall 24.

The exemplary canula 12 of FIG. 6 comprises a first fixing bulge 42 and a second fixing bulge 58 to fix the position of the canula 12 with respect to the thoracic cavity wall 24. For fixing the relative position in both directions, the outer diameter D1 of the intermediate portion 16 should be smaller than the outer diameter D2 of the first fixing bulge 42 and the outer diameter D3 of the second fixing bulge 58 as shown in FIG. 6.

In FIG. 6, the first fixing bulge 42 abuts on the inner surface 24i of the thoracic cavity wall 24 and can thereby inhibit the canula 12 from sliding out of the inserted position. The second fixing bulge 58 abuts on the outer surface 24o of the thoracic cavity wall 24 to thereby inhibit the canula 12 from sliding further into the pleural cavity 28.

For further fixation of the relative position of the canula 12 with respect to the thoracic cavity wall 24, the fixing plate 44 may abut on the outer surface 24o of the thoracic cavity wall 24 and allows fixing the position of the canula 12 relative to the thoracic cavity wall 24. For example, adhesive tape applied to flaps 44a, 44b of the semi-flexible fixing plate 44 and the outer surface 24o of the thoracic cavity wall 24 may inhibit relative movement (especially rotational movement) of the canula 12 with respect to the thoracic cavity wall 24. Hence, the exemplary needle assembly 10 may allow safe transport of the patient to an operating room with the canula 12 fixed in the inserted position.

The description of the preferred embodiments and the Figures merely serve to illustrate the invention and the beneficial effects associated therewith, but should not be understood to imply any limitation. The scope of the invention is to be determined solely by the appended claims.

LIST OF REFERENCE SIGNS 10 needle assembly
10a, 10b, 10c different needle assembly positions during insertion
12 canula
14 proximal end portion
16 intermediate portion
18 first curved portion
20 distal end portion
22 cutting end
22a cutting edge of the cutting end
24 thoracic cavity wall
24i, 24o inner/outer surface of the thoracic cavity wall
26a, 26b adjacent ribs
28 pleural cavity
30 lateral opening
32 blunt end piece
34 lung
36 adapter
38 flexible tube
40 pressure relief valve
42 first fixing bulge
44 fixing plate
44a, 44b flaps of the fixing plate
45 further curved portion
46 second curved portion
48 curved trajectory
50 pointed tip
52 spring
54 slanted portion of the cutting end
56 slot
58 second fixing bulge
D1 outer diameter of the intermediate portion
D2 outer diameter of the first fixing bulge
D3 outer diameter of the second fixing bulge
$F_a$ axial force
$F_c$ compressive resetting force
P1, P2 protruding/retracted position of the blunt end piece
A angular position of the tip
C position of the central axis of the canula at the cutting end T direction of the thoracic cavity with respect to the position of the central axis α angle between the direction of the thoracic cavity and the angular position.

The invention claimed is:

1. A needle assembly for relieving a pneumothorax and/or a hemothorax, the needle assembly comprising a canula, the canula comprising:
    a distal end portion comprising a cutting end for puncturing a thoracic cavity wall,
    a proximal end portion for removing a fluid or gas from a thoracic cavity,
    a first curved portion between the distal end portion and the proximal end portion,
    a second curved portion arranged between the first curved portion and the distal end portion, the second curved portion having a lower curvature than the first curved portion, and
    an intermediate portion between the first curved portion and the proximal end portion,
    wherein the needle assembly is characterized in that it further comprises:
    a first fixing bulge arranged between the first curved portion and the intermediate portion, wherein an outer diameter of the canula at the first fixing bulge is increased with respect to the diameter of the intermediate portion, said first fixing bulge being arranged such as to be placed at or close to the inner surface of the thoracic cavity wall, when the canula is inserted for relieving the pneumothorax, such as to prevent or to reduce the risk that the canula inadvertently slides out of its inserted position.

2. The needle assembly of claim 1, wherein the outer diameter of the first fixing bulge exceeds the diameter of the intermediate portion by at least 10% of the diameter of the intermediate portion.

3. The needle assembly of claim 1, wherein an angle between the orientation of the distal end portion and the orientation of the intermediate portion is between 30° and 120°.

4. The needle assembly of claim 1, wherein the cutting end comprises a bevel arranged at the distal end of the distal end portion, in particular a bevel with a pointed tip.

5. The needle assembly of claim 4, wherein the bevel tip is located on a cylindrical surface defined by the distal end portion of the canula at an angular position chosen such that the bevel tip is closest to the thoracic cavity wall when the canula is inserted for relieving pneumothorax, or at an angular position (A) that deviates from said angular position by 90° or less.

6. The needle assembly of claim 1, wherein a minimal diameter of the canula is greater than 2 mm.

7. The needle assembly of claim 1, wherein the distance between the tip of the distal end portion and the first curved portion of the canula is greater than 2.5 cm.

8. The needle assembly of claim 1, wherein the needle assembly comprises a blunt end piece, which is movable between
    a protruding position, in which the blunt end piece extends in a distal direction beyond the cutting end, and
    a retracted position, in which the blunt end piece is retracted behind the cutting end such as to expose the cutting end for a puncturing operation, and
    an elastic element for biasing said blunt end piece towards the protruding position.

9. The needle assembly of claim 1, wherein the canula and/or the blunt end piece further comprises a lateral opening close to the cutting end for removing a fluid and/or gas from the thoracic cavity.

10. The needle assembly of claim 1, wherein the canula comprises a second fixing bulge arranged between the intermediate portion and the proximal end portion, wherein an outer diameter of the canula is increased at the second fixing bulge, said second fixing bulge being arranged such as to be placed at or close to the outer surface of the thoracic cavity wall, when the canula is inserted for relieving the pneumothorax, such as to prevent or to reduce the risk that the canula inadvertently slides into the thoracic cavity.

11. The needle assembly of claim 10, wherein a length of the intermediate portion is greater than 2 cm.

12. The needle assembly of claim 1, wherein the needle assembly further comprises a fixing plate arranged on the canula and close to the proximal end portion, the fixing plate being arranged to abut on the outer surface of a patient's chest when the canula is inserted for relieving the pneumothorax, said fixing plate being suitable for fixing the relative position of the needle assembly to the thoracic cavity wall.

13. The needle assembly of claim 1, wherein the canula is made of surgical steel.

14. The needle assembly of claim 1, wherein the outer diameter of the first fixing bulge exceeds the diameter of the intermediate portion by at least 20% and at most 50% of the diameter of the intermediate portion.

15. The needle assembly of claim 1, wherein an angle between the orientation of the distal end portion and the orientation of the intermediate portion is between 60° and 120°.

16. The needle assembly of claim 4, wherein the bevel tip is located on a cylindrical surface defined by the distal end portion of the canula at an angular position chosen such that the bevel tip is closest to the thoracic cavity wall when the canula is inserted for relieving pneumothorax, or at an angular position (A) that deviates from said angular position by 60° or less.

17. The needle assembly of claim 1, wherein a minimal diameter of the canula is between 3 mm and 8 mm.

18. The needle assembly of claim 1, wherein the distance between the tip of the distal end portion and the first curved portion of the canula is between 3 cm and 6 cm.

19. The needle assembly of claim 8, wherein a spring constant of said elastic element is greater than 0.5 N/cm.

* * * * *